(12) United States Patent
Garćia Ramos

(10) Patent No.: US 11,559,202 B2
(45) Date of Patent: Jan. 24, 2023

(54) SYSTEM FOR INTEGRALLY MEASURING CLINICAL PARAMETERS OF VISUAL FUNCTION

(71) Applicant: E-HEALTH TECHNICAL SOLUTIONS, S.L., Barcelona (ES)

(72) Inventor: Eva Garćia Ramos, Barcelona (ES)

(73) Assignee: E-HEALTH TECHNICAL SOLUTIONS, S.L., Barcelona (ES)

( * ) Notice: Subject to any disclaimer, the term of this patent is extended or adjusted under 35 U.S.C. 154(b) by 862 days.

(21) Appl. No.: 16/348,853

(22) PCT Filed: Oct. 27, 2017

(86) PCT No.: PCT/ES2017/070721
§ 371 (c)(1),
(2) Date: May 9, 2019

(87) PCT Pub. No.: WO2018/087408
PCT Pub. Date: May 17, 2018

(65) Prior Publication Data
US 2019/0254519 A1     Aug. 22, 2019

(30) Foreign Application Priority Data
Nov. 10, 2016   (EP) ..................................... 16382521

(51) Int. Cl.
*A61B 3/02*     (2006.01)
*A61B 3/14*     (2006.01)
(Continued)

(52) U.S. Cl.
CPC ................ *A61B 3/18* (2013.01); *A61B 3/005* (2013.01); *A61B 3/0025* (2013.01);
(Continued)

(58) Field of Classification Search
CPC ........... A61B 3/112; A61B 3/113; A61B 3/18; A61B 3/0025; A61B 3/0033;
(Continued)

(56) References Cited

U.S. PATENT DOCUMENTS 9,706,910 B1 *   7/2017  Blaha ....................... A61B 3/10
2013/0095924 A1  4/2013  Geisner et al.
2016/0262608 A1  9/2016  Krueger

FOREIGN PATENT DOCUMENTS

WO     20160139662 A1     9/2016

OTHER PUBLICATIONS

International Search Report for PCT Application No. PCT/ES2017/070721, dated Feb. 7, 2018, in 4 pages.

* cited by examiner

*Primary Examiner* — Mahidere S Sahle
(74) *Attorney, Agent, or Firm* — Knobbe, Martens, Olson & Bear, LLP

(57) ABSTRACT

System for integrally measuring clinical parameters of the visual function including a display unit (20) for representing a scene with a 3D object having variable characteristics such as virtual position and virtual volume of the 3D object within the scene; movement sensors (60) for detecting the user head position and distance from the display unit (20); tracking sensors (10) for detecting the user pupils position and pupillary distance; an interface (30) for the user interaction on the scene; processing means (42,44) for analysing the user response based on the data coming from sensors (60,10) and the interface (30), with the characteristics variations of the 3D object; and based on the estimation of a plurality of clinical parameters of the visual function related to binocularity, accommodation, ocular motility and visual perception.

12 Claims, 4 Drawing Sheets

(51) Int. Cl.
  *A61B 3/10* (2006.01)
  *A61B 13/00* (2006.01)
  *A61B 3/18* (2006.01)
  *A61B 3/00* (2006.01)
  *A61B 3/024* (2006.01)
  *A61B 3/06* (2006.01)
  *A61B 3/08* (2006.01)
  *A61B 3/09* (2006.01)
  *A61B 3/113* (2006.01)
  *A61B 3/028* (2006.01)
  *A61B 90/50* (2016.01)

(52) U.S. Cl.
  CPC .......... *A61B 3/0033* (2013.01); *A61B 3/0041* (2013.01); *A61B 3/024* (2013.01); *A61B 3/028* (2013.01); *A61B 3/06* (2013.01); *A61B 3/066* (2013.01); *A61B 3/08* (2013.01); *A61B 3/09* (2013.01); *A61B 3/113* (2013.01); *A61B 3/00* (2013.01); *A61B 2090/502* (2016.02)

(58) Field of Classification Search
  CPC ....... A61B 3/0041; A61B 3/005; A61B 3/024; A61B 3/028; A61B 3/06; A61B 3/066; A61B 3/08; A61B 3/09; A61B 3/00; A61B 5/11; A61B 5/163; A61B 2090/502
  USPC .................. 351/206, 208–211, 239; 463/32; 600/558
  See application file for complete search history.

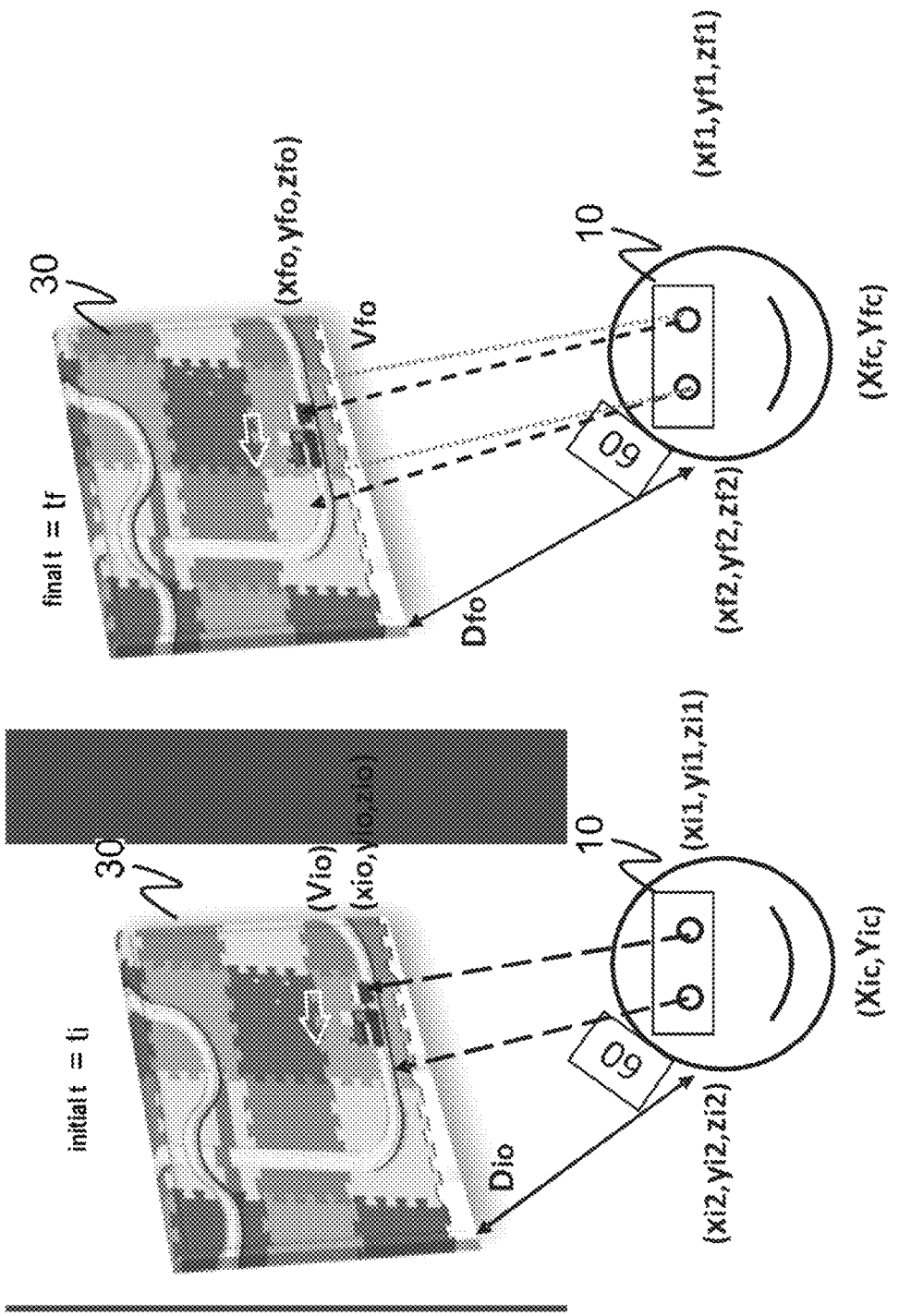

SYSTEM FOR INTEGRALLY MEASURING CLINICAL PARAMETERS OF VISUAL FUNCTION

CROSS-REFERENCE TO RELATED APPLICATIONS

This application is the U.S. National Phase under 35. U.S.C. § 371 of International Application PCT/ES2017/070721, filed Oct. 27, 2017, which claims priority to European Patent Application No. 16382521.9, filed Nov. 10, 2016. The disclosures of the above-described applications are hereby incorporated by reference in their entirety.

TECHNICAL FIELD OF THE INVENTION

The present invention belongs to the area of systems and methods for measuring clinical parameters of visual function. More particularly, it refers to techniques using virtual reality immersively so as to measure this type of parameters.

STATE OF THE ART

Currently, measuring this type of clinical parameters of visual function requires a clinical specialist having a session wherein the patient is tested through several tests and optotypes. It is common that the personal and manual component of the measuring process provides results being subjective, hardly reproducible and merely qualitative.

On the other side, the measurements are performed independently based on the visual function to be tested. This causes the results not to be valid sometimes, since influence of other factors is not considered. For example, it is known that patients usually compensate for a particular anomaly or impairment in the visual function thereof with the integral use of the other visual functions.

In short, currently the adaptation capacity of the patient is not taken under consideration and thus the actions intended to correct a concrete anomaly can result, in practice, in a global worsening of the patient vision. Furthermore, measurements and tests on the patient are affected by subjectivity of the specialist performing them, thus significantly limiting the reproducibility and consistency of the experimental results being obtained.

BRIEF DESCRIPTION OF THE INVENTION

The present invention refers to a system for integrally measuring ocular, oculomotor and visual function parameters, preferably in real time and generating therapy and training for visual function improvement.

For this purpose, tracking sensors which detect the position of the user pupils, a three dimension display unit (3D) reproducing certain scenes for the user with 3D objects having predetermined properties regarding size, shape, colour, speed, etc., are used which have been selected based on the type of test which is to be performed as part of the session. Movement sensors detect the user movements such that the display unit can adapt the scene and provide it with an immersive character.

The system also includes an interface which the user can interact with. In particular, the interface receives commands from the user to interact with the display system. These commands can be registered in many different ways (by means of control buttons, voice commands, gloves, etc.).

The system also implements processing means managing the display unit, the sensor and the interface in a coordinate manner. Thus, the user response to the visual stimuli generated in the display unit are detected by the sensor and transmitted to the processing means for measuring clinical parameters.

An important point in the present disclosure lies in the technology based on virtual reality which allows generating environments for interaction with the user. In particular, what is searched for is the capacity for immersing into the virtual environment. This is particularly interesting for creating conditions which are similar to the real ones for the user, and which thus allow reproduction thereof repeated times if desired. For that purpose, the display unit is required to be coupled to the movement sensors carried by the user. In some embodiments this can be virtual reality glasses, in others a 3D screen and polarized glasses. In any case, coupling the movement sensors and the display unit allows that the 3D image is shown being adapted to the person movement or position, making the user feel like moving along said virtual environment being displayed, that is, feel like being immersed therein, preferably with a minimum visual field of 60° so as to be able to suitably carry out with the evaluation, therapy and training of the visual function. In order to achieve the above, an accurate coordination is important between the elements taking part in a session. Thus, the user is firstly introduced with a 3D Virtual Reality environment intended for the user to be immersed therein. In said 3D environment, some 3D objects will be displayed by way of "optotypes" which are intended to act as the stimuli upon which the user must focus their sight and which are related to the test intended to be performed.

BRIEF DESCRIPTION OF THE FIGURES

FIGS. 3A, 3B show an example of a measurement from a user having a dysfunction that is looking at a scene with a moving 3D object.

DETAILED DESCRIPTION OF THE INVENTION

An exemplary non-limiting embodiment is explained in further detail with reference to the previous figures.

Figure 1:
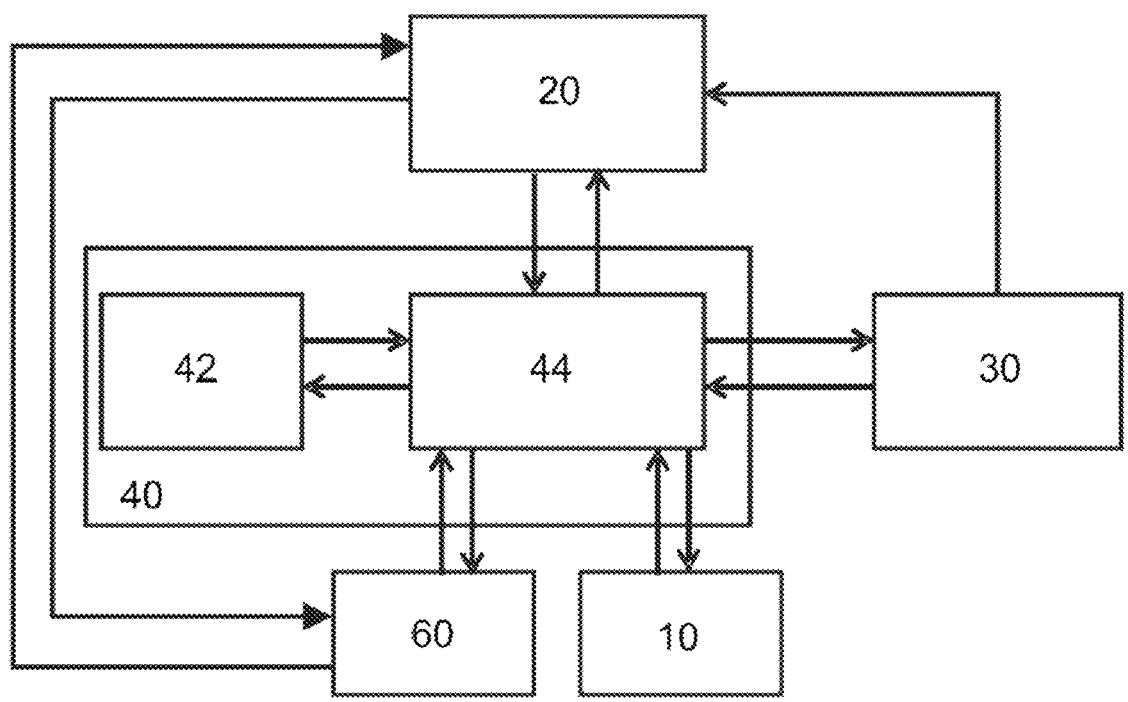
FIG. 1 shows a simplified block diagram according to a possible embodiment of the invention.

FIG. 1 illustrates a system for integrally measuring clinical parameters of the visual function in real time, including several components. There is a tracking sensor 10 which is used for periodically detecting the position of the user's pupils. Thereby, not only direction changes but also speed can be measured. Generally, the tracking sensor 10 allows measuring multiple parameters based on the particular test being performed in the session. FIGS. 2 and 3 illustrate this aspect of the invention in further detail. For example, the tracking sensor 10 can take values for the position of the right and left eye, for the position of the object the user is looking at (through both eyes and separately), eye-sensor distance, pupil size, interpupillary distance, speed of the eye movement, etc. Generally, in order to perform the measuring operation, the tracking sensor 10 comprises a pair of cameras intended for being focused on the user's eyes and capturing their movement and position. This requires a sampling frequency which is high enough to capture the fast movements of the eyes. It must also calculate the position within the generated virtual environment where the user is looking at. The tracking sensor 10 is essential for a correct optometric measurement. A great amount of dysfunctions are detected by means of anomalous movements of the eyes against several stimuli. For clarity reasons, FIGS. 2 and 3 show examples of how the measurements taken by sensors 10, 60 are associated to a visual condition of the user, with or without a possible dysfunction, respectively.

A display unit 20 with 3D immersive capabilities reproduces or projects for the user scenes with depth features including 3D objects having pre-determined properties regarding size, shape, colour, location in the scenery, distance from the user, standing still or in movement, etc. These scenes including 3D objects work as optotypes and can be selected in the system according to the type of test intended to be performed which allow generating certain visual stimuli in the user. Thus, a plurality of scenes can be designed for the user having different visual challenges and stimuli, either for evaluation, therapy or training of the visual function.

The system also includes an interface 30 for the user interaction. Particularly, the interface receives commands from the user to control the display unit 20 and other elements of the system. The interface 30 in turn can also transmit instructions for the test to the user. Thus, the system can measure the response to the user actions (movement, position in the 3D environment, pressing buttons, etc.).

The system also includes processing means 40, preferably implemented as a server 42, and a terminal 44 which coordinately share management of the display unit 20, the sensor 10 and the interface 30 control, such that the visual responses from the user may be detected by the sensor 10 and transmitted to the server 42 for measuring clinical parameters of the visual function. Furthermore, the display unit 20 allows adaptation of the 3D image represented according to the user movement. The display unit 20 can include a dissociating system (such as polarized glasses or the like).

The test is preferably started through the 3D interface. While visualizing a concrete scene, the user visual stimuli which have been detected by sensor 10 at a given time, are associated to the 3D objects represented at that time in the display unit 20. These changes in the position of the user pupils are detected and combined with the movements made by the user's head which are detected by means of a movement sensor 60. Coupling the movement sensors 60 and the display unit 20 allows showing the 3D image being adapted to the movement or the position of the person, making the user feel like actually moving through said virtual environment they are visualizing, that is, like being immersed therein.

Data are processed and the properties of the 3D objects are associated to the generated stimuli detected by sensors 10, 60. This allows measuring clinical parameters of the visual function under reproducible and controllable conditions. Thus, by means of the suitable processing of the data being obtained, the visual behaviour of the user, eyes movement, convergence, . . . etc., can be known. Also, the clinical parameters of the visual function can be compared to an expected range so as to asses if there is any problem.

As it has been indicated, together with the 3D objects visualization in the display unit 20, the tracking sensor 10 tracks the user look in said Virtual Reality environment. The tracking sensor 10 registers:

The position of the eyes (left and right).
Location to which each eye looks at (separately).
Location at which the user looks by using both eyes in combination in the 3D environment.

Also at the same time, instructions can be shown for guiding the users by explaining what they must do at every moment. These instructions can be by way of text or audio through an interface 30. Said interface 30 also allows the user to interact with 3D objects from the scene being represented by the display unit 20. The interaction with the user starts at that moment and the responses given to the stimuli being shown, that is the measurements, must be registered.

These responses of the user can be, for example, among others, by means of:

Movement of the device (in any direction in the space).
Position of the device within the Virtual Reality environment.
Pressing the buttons of the device.
Voice commands.

In the situation described above, for the previous tasks the process is preferably performed in a client terminal 44, although these have been provided (downloaded) from an outer server 42. A distributed environment allows reducing the technical requirements of the terminal 44, a centralized control of the tests performed in different users, access to statistical data, etc. For example, the heaviest operations and calculations can be performed in the server 42 offloading processing workload from the terminal 44. Likewise, the characteristics which may be established for a test can be defined from the server 42:

The Virtual Reality environment to be used.
The 3D objects and characteristics thereof (size, distance, colours, movement, . . . )
What instructions to give the user.
When to capture information with the tracking sensor 10.
When to capture information with the user interface 30.
Which data to register and output as a result of the execution task.

Regarding the data to be registered, there are data coming from sensors 10, 60 and also through the interaction with the user with the interface 30.

Once the whole local treatment of data has finished, these are grouped and sent to the server 42 for storage and subsequent analysis thereof. Thus, statistics, new tests, recommendations, therapies, etc., can be performed.

For example, it can be verified if the values obtained for given parameters are within the tolerance limits according to scientific studies stored in the server 42. On the other side, a new scene can be designed as recommendation which acts as a therapy or training for improving some of the functionalities for which the test provided a worse result.

Figure 2B:
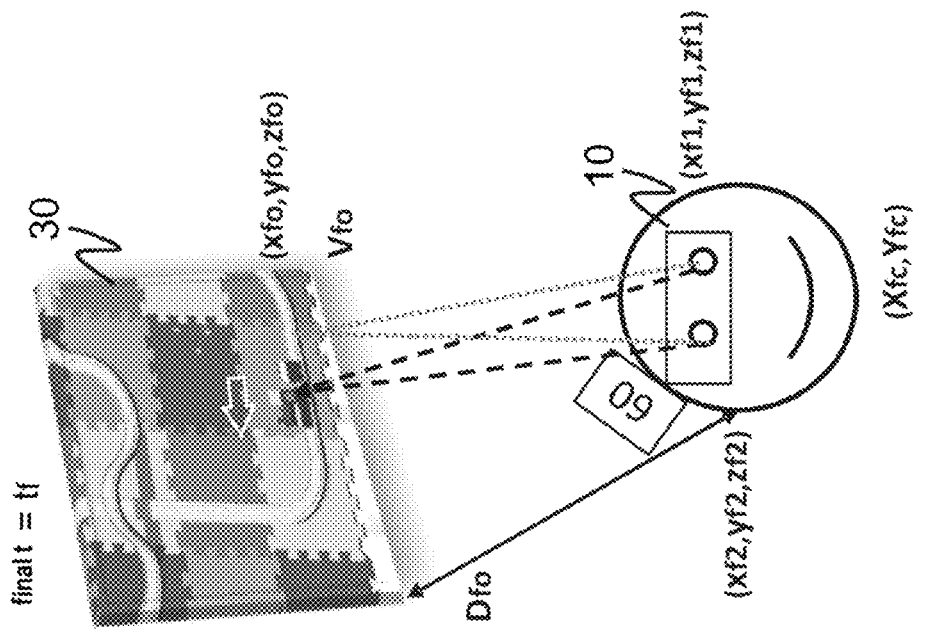
FIGS. 2A, 2B show an example of a measurement from a healthy user looking at a scene with a moving 3D object.
Figure 2A:
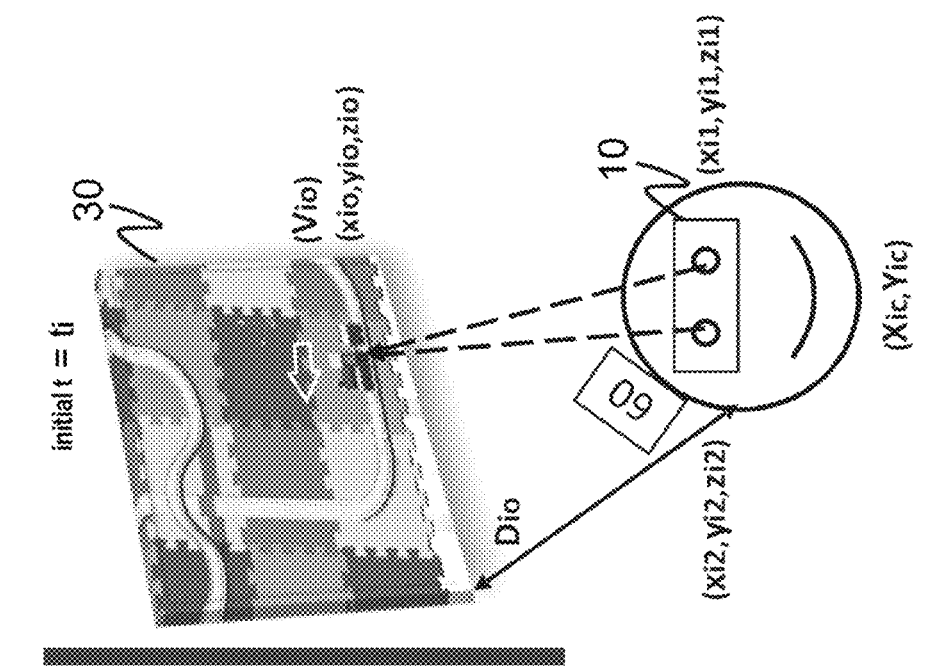

FIGS. 2A and 2B illustrate an example in which a user interacts with the system at two instants of time. At an initial instant $t=t_i$, the system represents a 3D model in the display unit 30 corresponding to a train running along a railway.

The user carries a movement sensor 60 for registering, at both time instants, the head movements $(X_{ic}, y_{ic})$, $(X_{fc}, Y_{fc})$ and the distance $D_{ic}$, $D_{fc}$ with the display unit 20. Similarly, a tracking sensor 10 registers the pupillary movements of the user at both time instants, providing more information about the position of both pupils. Right: $(x_{i1}, y_{i1}, z_{i1})$, $(x_{f1}, y_{f1}, z_{f1})$; Left: $(x_{i2}, y_{i2}, z_{i2})$, $(x_{f2}, y_{f2}, z_{f2})$.

On the other hand, the display unit 20 represents the 3D object in two different virtual positions $(x_{io}, y_{io}, z_{io})$, $(x_{fo}, y_{fo}, z_{fo})$ and with two different volumes at each time instant $V_{io}$, $V_{fo}$. Other properties such as the colour of the 3D object may vary as a function of the test to be performed in the session.

When processing of the above values takes place, it is checked that the user's eyes are suitably coordinated with the 3D object movement in the scene. The visual behaviour corresponds to a healthy individual.

FIGS. 3A and 3B schematically illustrate the above case where the visual behaviour of the user does not respond appropriately to the stimuli. As it can be seen, in FIG. 3A, the user does not align correctly the visual axis of their left eye $(x_{i2}, y_{i2}, z_{i2})$ onto the object of interest $(V_{io})$, revealing a limitation of their binocular vision (strabismus). In this case, the deviation angle (FIG. 3B) is kept constant by moving the object of interest $(V_{fo})$, indicating a comitant condition, that is, it has the same deviation angle in different positions of the look. This information is critical to determine the severity of the condition as well as that of the type of recommendation of visual therapy in order to re-establish the binocularity of the subject.

Clearly, the scene chosen is just an example. Others could be an aquarium having fish with different shapes, colours and size which continue appearing and disappearing; a road with a car moving closer to the user; holes with moles coming out randomly, etc. In these scenes, the parameters can be measured objectively and also all together (without underestimating an existing influence between one another).

Figure 4:
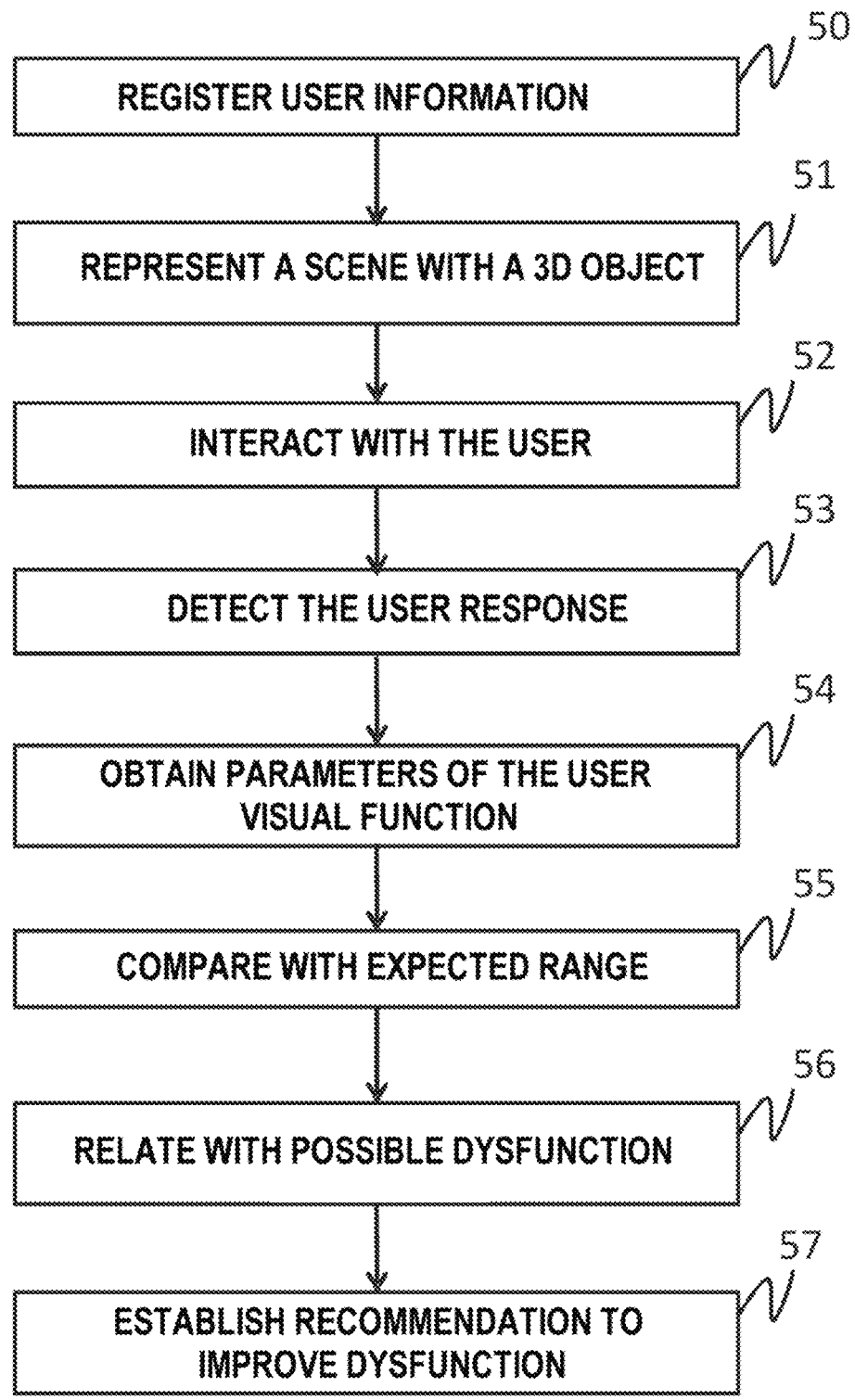
FIG. 4 shows a summary diagram with the general steps being implemented in an embodiment.

FIG. 4 briefly illustrates a possible sequence of actions during the operation of the system for a test. In a first step 50 personal relevant information of the user is registered. Preferably, the data introduced are: sex, age, habits, etc., for which the interface 30 can be used. The user, by means of the terminal 44, makes a request to the server 42 as a client, and the application associated to the type of test being selected is installed.

The user places in front of the display unit 20, instructions are given to the user through the interface 30 or the display unit 20 so as to place the tracking sensor 10 correctly or to sit in the appropriate position with respect to the display unit according to the movement sensor 60. Then, at step 51 a scene is represented relating to the test being selected, with one or several 3D objects the properties of which change over time or with the user interaction.

The user and the display unit interact through the interface 30 at step 52. In general, the user can be given instructions during the test, both using graphics and audio. For example, the interface 30, can incorporate any element for making easier the user interaction with 3D objects from the scene 30 represented in the display unit 20.

Sensors 10, 60 detect the values at step 53 while the scene is being reproduced. These data must be sent with a minimum latency to the terminal 44.

Terminal 44 receives the captured data and pre-processes and sends them to the server 42 so as to obtain clinical parameters values of the visual function at step 54.

Once the test or the session with different tests, is finished, terminal 44 sends the data being obtained to the server 42 for storage and further processing thereof. Particularly, the parameters are compared to an expected range for the user profile at step 55.

When the server 42 has processed the data being obtained it relates them with a possible dysfunction at step 56.

Finally, the server generates possible recommendations to improve the dysfunction at step 57 and transmit those to terminal 44 in order to show them to the user together with the results being obtained.

Thanks to the technology being used, the tests are performed objectively and integrally, as well as in customized manner, and they allow identification of different visual dysfunctions. Specially, those limiting the capacities for eye alignment over the object of interest (convergence insufficiency, excess of divergence, inflexibility of vergences), or focusing capacity (accommodation insufficiency, excess of accommodation, inflexibility of accommodation), or limitation upon changing look from one object to the other (saccadic eye movements) or tracking of an object (smooth pursuit movements) or the visuoperceptual abilities required for identifying and managing information about our environment. All of them can be assessed and trained in a customized manner (not only based on the conditions under which the test was performed, but also on the development of each working session). On the other hand, a great variety of visualizations can be provided for the same exercise, which allows a better adaptation to the daily visual demands and keeping the interest and attention in doing the exercises.

It should be noted that the present invention is not only useful for identifying dysfunctionalities, but also for training the physical and technical activities of healthy users by means of visual stimuli and challenges. This can be directly applied on sport people and children, and it can be broaden both to specific professional (drivers, pilots, . . . ) and amateur (abilities in handling miniatures, entertainment games, . . . ) visual demands.

It should be noted that one of the advantages the present disclosure features is that only a reduced space is required for accommodating the necessary devices. For example, for an embodiment using a screen configured as a display unit 20, everything can be placed on a table at a distance from the user, who will be preferably sitting, between 50 cm and 1 m, together with a computer as an element being part of the processing means 40. The rest of the elements are carried by the user in head and hands (control devices, gloves, . . . ). Even less element, in case an embodiment in which the display unit 20 is a pair of VR glasses.

What is claimed is:

1. A system for integrally measuring clinical parameters of the visual function comprising:
    a display unit configured for representing a scene wherein at least a 3D object on the scene has variable characteristics for promoting a visual response in the user, wherein said variable characteristics include at least the virtual position (Xo,Yo,Zo) and the virtual volume (Vo) of the 3D object within the scene;
    a plurality of movement sensors configured for detecting the user head position (Xc,Yc) and distance (Dc) from the display unit;
    a plurality of tracking sensors configured for detecting the user pupils position (xp, yp, zp) and pupillary diameter (dp), wherein the plurality of tracking sensor register pupillary movements of a right eye and a left eye of the user corresponding to a movement of the 3D object in the scene;
    an interface configured for producing at least variations on the virtual position and the virtual volume of the 3D object within the scene and for allowing the user to interact on the scene;
    a processor configured for analyzing the user response based on:
    associating the user data measures coming from the sensors and user interaction commands on the scene of the interface to the features variation of the 3D object represented in the display unit;
    estimating a plurality of clinical parameters of the user visual function;
    comparing the clinical parameters to a stored range of reference values; and establishing a possible visual dysfunction based on the comparison.

2. The system according to claim 1, wherein the characteristics are variable as a function of time according to a pre-determined programming.

3. The system according to claim 1, wherein the variable characteristics also include color of the 3D object.

4. The system according to claim 1, wherein the characteristics are variable as a function of the user interaction through the interface.

5. The system according to claim 4, wherein the interface comprises at least one of the following: a digital pen, a glove, a control device or the like.

6. The system according to claim 1, wherein the display unit comprises a 3D screen.

7. The system according to claim 1, wherein the display unit comprises Virtual Reality glasses.

8. The system according to claim 1, wherein the display unit comprises a dissociating system.

9. The system according to claim 8, wherein the comparison to a range of reference values is realized based on the user profile which includes at least age information.

10. The system according to claim 1, wherein the processor comprises a client terminal and a server, wherein the client terminal is configured for receiving and processing the data measured by sensors and sending them to the server.

11. The system according to claim 10, wherein the server is configured for comparing the values with a data base having reference values.

12. The system according to claim 1, wherein the visual function of the clinical parameters refers to at least one of the following: binocularity, accommodation, ocular motility or visual perception.

* * * * *